Aug. 6, 1963 N. H. COLE, SR Plant Pat. 2,272
ILEX (HOLLY) PLANT
Filed Nov. 20, 1961
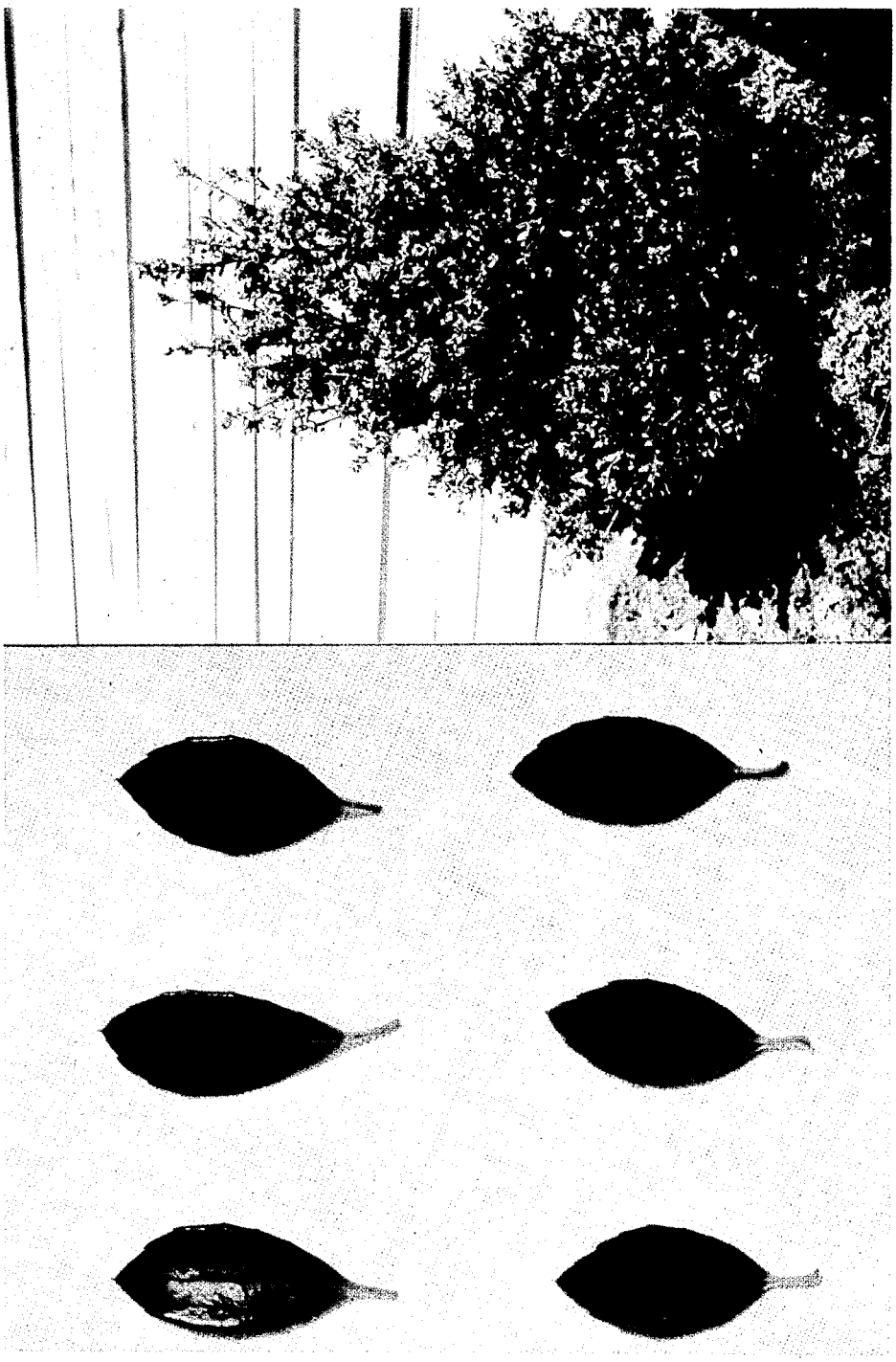
INVENTOR
Norman H. Cole, Sr
BY Robb & Robb
ATTORNEYS United States Patent Office Plant Pat. 2,272
Patented Aug. 6, 1963

2,272
ILEX (HOLLY) PLANT
Norman H. Cole, Sr., R.R. 2, North Tazewell, Va.
Filed Nov. 20, 1961, Ser. No. 153,769
1 Claim. (Cl. Plt.—65)

The present invention relates to a new and distinct variety of Ilex (holly) plant which was discovered by me as a cultivated bud sport or mutation of the variety of Japanese holly botanically known as *"Ilex crenata convexa"* (unpatented).

At the time of my discovery of this new variety, I was growing a block of plants of the regular variety of Japanese holly botanically known as *"Ilex crenata convexa"* on my cultivated property located at Springville, in Tazewell County, Virginia, these plants numbering approximately one thousand (1,000), and having been set out by me as rooted cuttings. In the course of one of my regular field inspections of these plants, my attention was attracted to one particular plant which exhibited unusual characteristics and distinguished it from all of the other plants in this entire block. The principal features which attracted my attention were the more upright habit of growth of the plant and the darker green color of its foliage. I thereupon carefully preserved this plant and continued my observations thereof, as well as asexually reproducing the same by cuttings on my property at Springville, Virginia. These asexual reproductions conclusively established that the unusual characteristics referred to above, together with other differentiating features, were fixed and capable of being transmitted through succeeding asexual propagations.

As the result of my prolonged observations and tests of the original plant and the progeny thereof obtained by propagating the same by cuttings, I am convinced that my new variety represents a unique combination of outstanding characteristics which definitely distinguish the same from its parent, as well as from all other species and varieties of which I am aware. The following constitute the principal features of this unique combination:

(1) A naturally broad pyramidal form of the plant which requires little or no trimming to maintain the pyramidal form;

(2) A slightly serrated and relatively flat form of the leaves which are somewhat similar to the leaves of the variety of Japanese holly botanically known as *"Ilex crenata microphylla"* (unpatented), but which are not as pointed at the apex, and said leaves being flatter than the normally cupped leaves of the variety known as *"Ilex crenata convexa"*;

(3) An attractive deep and rich green color of the leaves which is retained throughout the winter, and being both deeper and richer than the color of the leaves of the parent variety; and (4) Unusually good resistance to cold and wind, as evidenced by the fact that the new variety has been grown successfully at altitudes of around 3,000 feet above sea level where it was subject to cold and windy weather conditions, yet survived temperatures as low as 20° F. below zero, and exhibited practically no leaf or twig damage.

The accompanying drawing shows a typical specimen plant of my new variety, as well as typical specimens of the foliage on a somewhat enlarged scale, all as depicted in color as nearly true as it is reasonably possible to make the same in a color illustration of this character.

The following is a detailed description of my new variety, with color terminology in accordance with Nickerson's Color Fan, published by Munsell Color Company, Inc., of Baltimore, Maryland, except where general color terms of ordinary dictionary significance are obvious:

Type: Hardy; attractive evergreen; for use in landscape and hedge plantings.

Class: *Ilex crenata* Thunb.

Parentage: Sport or mutation of *"Ilex crenata convexa."*

Location where grown and observed: Springville, Virginia, and Bluefield, West Virginia.

Habit of growth: Much-branched shrub ranging from globose to spreading in form when young, but becoming more upright within three years when grown from cuttings, and attaining a height of at least 2 meters, combined with a distinctive pyramidal form, within seven years; vigorous.

Branches: Upright. Color—Moderate Olive Green, Plate 2.5GY 4/3.

Foliage:

*Leaves.*—From oblanceolate to obovate; cuneate; mucronate; crenate-serrulate; from 12 to 26 mm. long and from 5 to 10 mm. wide; from 13 to 19 teeth; smooth on upper surface; medium glossy; leathery. Petiole—from 2 to 4 mm. long; color—dark green. Color: upper side—from moderate Olive Green, Plate 7.5GY 4/4 to Dark Grayish Green, Plate 10GY 3/2; under side—from Strong Yellow Green, Plate 5GY 6/8 to Moderate Yellow Green, Plate 5GY 5/6.

Flowers: Staminate.

*Blooming date*—April and May.

*Inflorescence.*—2 to 8 flowered.

*Petals.*—Orbicular; from 0.15 cm. to 0.20 cm.

Hardiness: Good resistance to cold and wind.

I claim:

A new and distinct variety of Ilex (holly) plant of the evergreen class, substantially as herein shown and described, characterized particularly as to novelty by a naturally broad pyramidal form of the plant which requires little or no trimming to maintain its shape, relatively flat and slightly serrated leaves of deep, rich green color, and exceptionally good resistance to cold and windy weather.

No references cited.